(12) United States Patent
Chan

(10) Patent No.: US 8,635,045 B2
(45) Date of Patent: Jan. 21, 2014

(54) METHODS FOR AUTOMATIC PEAK FINDING IN CALORIMETRIC DATA

(75) Inventor: Heather Yee-Mei Chan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 220 days.

(21) Appl. No.: 12/957,226

(22) Filed: Nov. 30, 2010

(65) Prior Publication Data

US 2012/0136616 A1    May 31, 2012

(51) Int. Cl.
*G06F 15/00* (2006.01)
(52) U.S. Cl.
USPC .......................................... 702/136
(58) Field of Classification Search
USPC .......................................... 702/136
See application file for complete search history.

(56) References Cited

U.S. PATENT DOCUMENTS

| | | | |
|---|---|---|---|
| 6,944,549 B2 | 9/2005 | McClure | |
| 2010/0100336 A1 | 4/2010 | Wright et al. | |

OTHER PUBLICATIONS

Matthew W. Freyer, Isothermal Titration Calorimetry: Experimental Design, Data Analysis, and Probing Macromolecule/Ligand Binding and Kinetic Interactions, Department of Chemistry and Biochemistry Northern Arizona University FlagstaV, Arizona 86011, Methods in Cell Biology, vol. 84 0091-679X/08, Copyright 2008, Elsevier Inc. p. 79-113.*
Kirk L. Shanahan, systematic error in mass flow calorimetry demonstrated, 0040-6031/02/$—see front matter # 2002 K.L. Shanahan. Published by Elsevier Science B.V. All rights reserved, p. 95-100.*
Search Report and Written Opinion from corresponding PCT Application No. PCT/EP2011/070950 dated Mar. 2, 2012.
Anderson et al., "Computer analysis of unresolved non-Gaussian gas chromatograms by curve-fitting", Database Inspec [Online] The Institution of Electrical Engineers, vol. 42, No. 4, pp. 434-440, Apr. 1970.
Budaguan et al., "Calorimetric investigation of structural processes in porous silicon", Journal of Non-crystalline Solids, vol. 204, No. 2, pp. 169-171, Sep. 1, 1996.
Lee et al., "Accuracy Improvement in Peak Positioning of Spectrally Distorted Fiber Bragg Grating Sensors by Gaussian Curve Fitting", Applied Optics, vol. 46, No. 12, pp. 2205-2208, Apr. 20, 2007.

* cited by examiner

*Primary Examiner* — Tung S Lau
(74) *Attorney, Agent, or Firm* — Jenifer Haeckl

(57) ABSTRACT

In one embodiment, a method for automatically determining a position of one or more calorimetric peaks in a set of calorimetric data is provided. The method comprises a) providing a non-linear fit for the calorimetric data, b) calculating a residual by subtracting the non-linear fit from the calorimetric data, c) calculating an error based on the residual, d) comparing the error with a predetermined error, and e) providing another non-linear fit if the error is greater than the predetermined error.

13 Claims, 3 Drawing Sheets

METHODS FOR AUTOMATIC PEAK FINDING IN CALORIMETRIC DATA

BACKGROUND

The invention relates to methods for analyzing calorimetric data obtained from calorimetric instrument, and in particular, to methods for automatically identifying peaks and/or peak positions in calorimetric data.

Differential scanning calorimetry (DSC) is a thermo-analytical technique that is used for thermal analysis. DSC is used across a range of applications, both as a routine quality test and as a research tool. For example, DSC may be used to study stability of compounds, security screening, drug analysis or drug analysis.

In calorimetric applications, several peak-finding methods are used to identify multiple peaks in calorimetric data. Most of these methods use user-supplied initial guesses for the number of peaks and each peak location. In the manual procedure, the user visually evaluates the single-peak fit and decides whether an additional peak might exist. However, in low-signal/high-noise data, multiple peaks become indistinguishable to the user, forcing the user to assume a single peak. Further, a manual procedure also introduces user-related variability.

Therefore, it would be desirable to provide automated methods for analyzing calorimetric data that requires minimum user input to determine number and location of peaks in the calorimetric data, including peaks that are not visible to the user.

BRIEF DESCRIPTION

In one embodiment, a method for automatically determining a position of one or more calorimetric peaks in a set of calorimetric data is provided. The method comprises a) providing a non-linear fit for the calorimetric data, b) calculating a residual by subtracting the non-linear fit from the calorimetric data, c) calculating an error based on the residual, d) comparing the error with a predetermined error, and e) providing another non-linear fit if the error is greater than the predetermined error.

In another embodiment, a method for automatically determining a position of one or more calorimetric peaks in a set of calorimetric data is provided. The method comprises a) providing a first non-linear fit for the calorimetric data, b) determining a first residual by subtracting the first non-linear fit from the calorimetric data, c) calculating a first error based on the first residual, d) providing a second non-linear fit for the calorimetric data, e) determining a second residual by subtracting the second non-linear fit from the calorimetric data, f) calculating a second error based on the second residual, g) comparing the first and second errors, and f) selecting the non-linear fit corresponding to a lower error.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
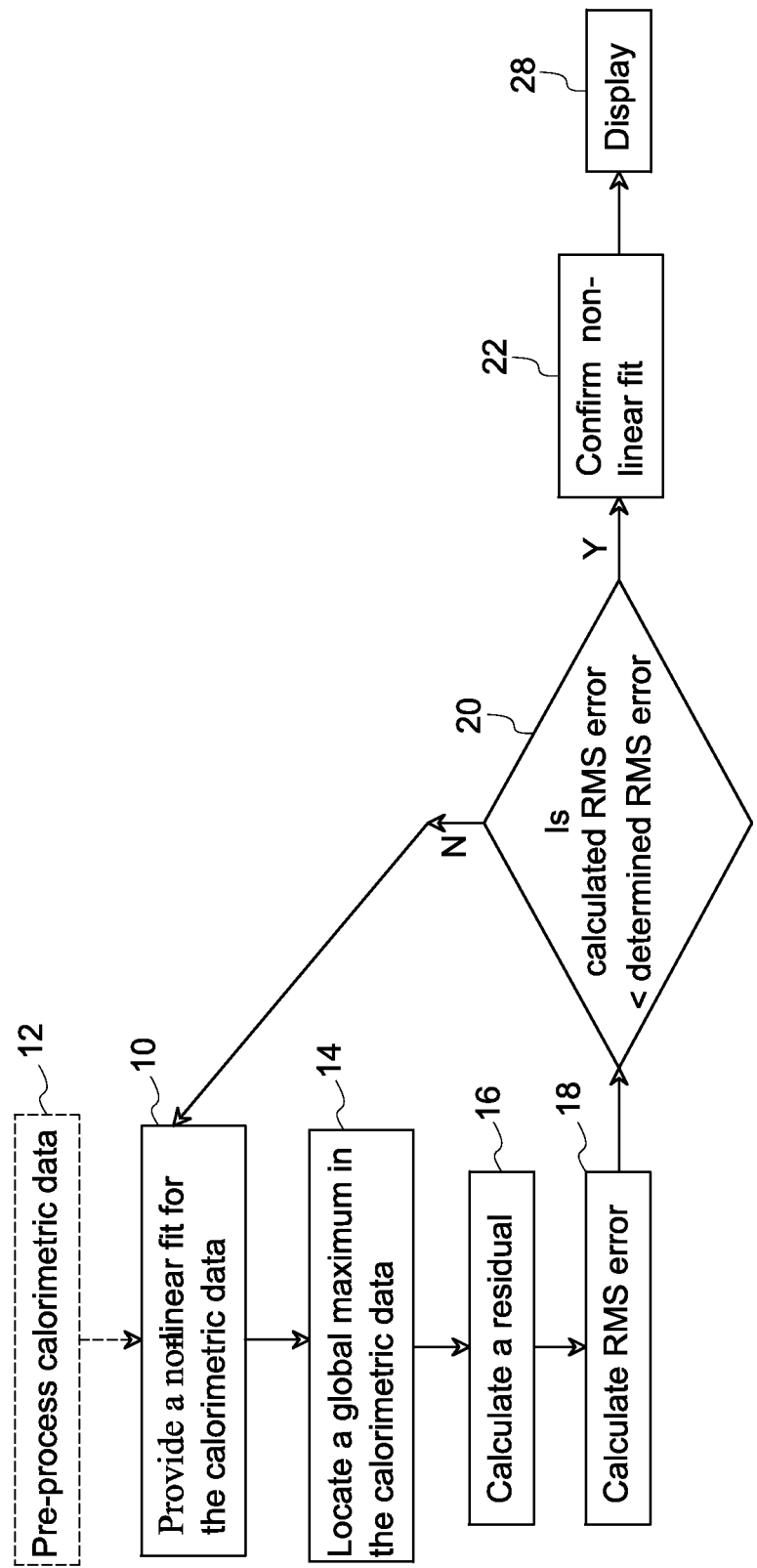
FIG. 1 is a flow chart for an example method for automatic peak fittings for calorimetric data.

One or more examples of the methods of the invention relate to analyzing calorimetric data with minimal or no user input for determining the number and location of calorimetric peaks, including peaks that are not easily visible to human eye. In certain examples, the method for automatically determining a position of one or more calorimetric peaks comprises performing a non-linear fit for the position of the maximum peak, subtracting the non-linear fit from the calorimetric data to obtain a residual, calculating an error based on the residual; comparing the error with a predetermined error; and providing another non-linear fit if the error is greater than the predetermined error.

Although one or more examples of the methods are used to analyze calorimetric data, the methods may accommodate and model other data types having similar distribution. The peaks in the calorimetric data may be determined using the method where the peaks are otherwise invisible to a user or operator. In one example, the peaks may be invisible due to high noise levels in the data. The methods may be modified to suit the type of data to be analyzed. For example, instead of calculating root mean square error, other possible evaluation metrics include mean squared error, mean absolute error, chi-squared error, correlation coefficient, or coherence error.

In one embodiment, a theoretical expression used to model the curve may include thermal models, such as but not limited to, an independent two state transition model, a non-two-state, or a non-independent (i.e. cooperative) model. In one example, the non-linear fit may be population based. For example, the shape of the peak may be related to the number of proteins that unfold at a given point of time during the course of the experiment, the peak may occur at the point where 50 percent of the proteins have been unfolded, thereby representing an integral change in enthalpy. Non-limiting examples of non-linear fit may include Gaussian, Cauchy, weighted mixture of Gaussian and Cauchy profile, asymmetric Gaussian, monotonic transition from Gaussian to Cauchy profile). Equations 1-3 are examples of a theoretical expression for modeling the curve. The model is based on the two state transition model. The equations 1-3 comprise parameters specific to the calorimetric system.

$$C_p(t) = B_o + B_1 T + \left[ \frac{K_A(T)\Delta C_{pA}}{1 + K_A(T)} + \frac{K_A(T)\Delta H_A(T)^2}{(1 + K_A(T))^2 RT^2} \right] \quad \text{Eq. 1}$$

$$\Delta H_A(T) = \Delta H_{mA} + \Delta C_{pA}(T - T_{mA}) \quad \text{Eq. 2}$$

$$K_A(T) = \exp\left\{ \frac{-\Delta H_{mA}}{RT}\left(1 - \frac{T}{T_{mA}}\right) - \frac{\Delta C_{pA}}{RT}\left(T - T_{mA} - T\ln\frac{T}{T_{mA}}\right) \right\} \quad \text{Eq. 3}$$

where $B_o$, $B_1$ are constants, domains A and B refer to different stages in which proteins may unfold, T is temperature, $T_{mA}$ is the temperature at which 50 percent of the proteins have unfolded in domain A, Cp is a molar heat capacity, $\Delta$Cp is a change in molar heat capacity, $K_A$ is an equilibrium constant for domain A, $\Delta H_A$ is a change in a molar heat enthalpy for domain A, $\Delta C_{pA}$ is a change in a molar heat capacity for domain A, and $\Delta H_{mA}$ is a change in a molar heat enthalpy for domain A at temperature $T_{mA}$.

FIG. 1 is a flow chart of an example of a method of the invention. At step 10, the method begins by providing a non-linear fit for the calorimetric data. Non-limiting examples of the non-linear fit may include Levenberg-Marquardt algorithm, or a polynomial fit. The calorimetric data may be directly received from a calorimetric device. The calorimetric data may also be accessed from a memory or a data file comprising data previously collected from, for example, an experimental setup.

Optionally, at step 12, the experimental data may be pre-processed. For example, the experimental data may be pre-processed to subtract a baseline. It may not always be required to have a baseline subtraction from the calorimetric data. The need for pre-processing step may depend on the level of complexity of the system. Pre-processing may be performed to reduce the noise level in the experimental data. Alternatively or in addition, the pre-processing may be performed to estimate the noise level in the experimental data. The calorimetric data may comprise a combination of calorimetric signal and baseline. Baseline features may be subtracted from the data to obtain a signal having reduced noise. This signal with reduced noise may then be used for fitting a non-linear curve. The calorimetric data may be processed to reduce the noise. In one embodiment, the method for automatically removing baseline features from the calorimetric data comprises repeatedly fitting one or more polynomial functions one at a time to the baseline, subtracting the best fit polynomial function from the calorimetric spectrum so as to provide a current baseline-corrected spectrum, evaluating the quality of the fit, as measured by a sum of squared residuals (SSR), and proceeding until SSR changes, from iteration to iteration, by less than a predetermined percentage of its original value.

At step 14, a maximum peak in the calorimetric data may be located based on the fitted non-linear fit. The maximum peak may also be referred to as "maxima" or "global maxima". In one embodiment, the maxima may be located by calculating enthalpy change with respect to temperature. Optionally, the position of the maxima may be stored. In one example, a position of the maxima and the value of the molar enthalpy at the maxima may be stored or displayed. The position of the maxima may be determined with respect to time or temperature or both.

At step 16, a residual may be determined for the non-linear fit. The residual may be obtained by subtracting the non-linear fit from the experimental data. The residual may be sum of all the residuals at various locations on the experimental data. In one embodiment, the residual may be determined by subtracting an area under the fitted curve from an area under the calorimetric data curve.

At step 18, an error is calculated based on the residual. In one embodiment, the error is a root mean square (RMS) of the residual.

At step 20, the calculated RMS error for the non-linear fit is compared with a determined RMS value. If the RMS error for the fitted peak is less than the determined RMS error, the fitted curve is accepted (step 22).

If the RMS error is more than the determined RMS error, next non-linear fit may be applied to the calorimetric data and steps 10, 14, 16, 18 and 20 may be repeated whereby RMS error is calculated and compared to the determined RMS error until the RMS error is equal to or less than the determined RMS error. The method is repeated for finding subsequent peaks and providing non-linear fits for the subsequent peaks. The process is repeated till the residual value is below a certain determined residual value, and the peaks are identified and non-linear fits are provided for the same. In one example, if the calculated RMS is greater than the determined RMS, one more peak is fitted, if after fitting the peak, RMS is less than or equal to determined RMS, the number of peaks is the number of peaks fitted with the RMS value being at the lowest.

In another example, if no RMS threshold is set, the number of peaks is the number of peaks fitted with the RMS value being at the lowest. Assuming that the RMS value of any non-linear fit is not less than the standard deviation of the noise, the determined RMS value may be selected by estimating the standard deviation over a relatively flat (linear) portion of the data. In one example, the calculated RMS error may be relatively greater than the determined RMS value (scaling factor >1) but not so large that less ideal fits may be accepted. The determined RMS value enables providing a closest non-linear fit for the calorimetric data while avoiding unnecessary inference of undesired peaks for the calorimetric data. The determined RMS value prevents the algorithm from searching through several peaks if the required number of peaks has already been discovered.

The determined RMS error value may be decided by the user. Alternatively, the determined RMS may be selected by the system depending on the type of DSC event.

Figure 2:
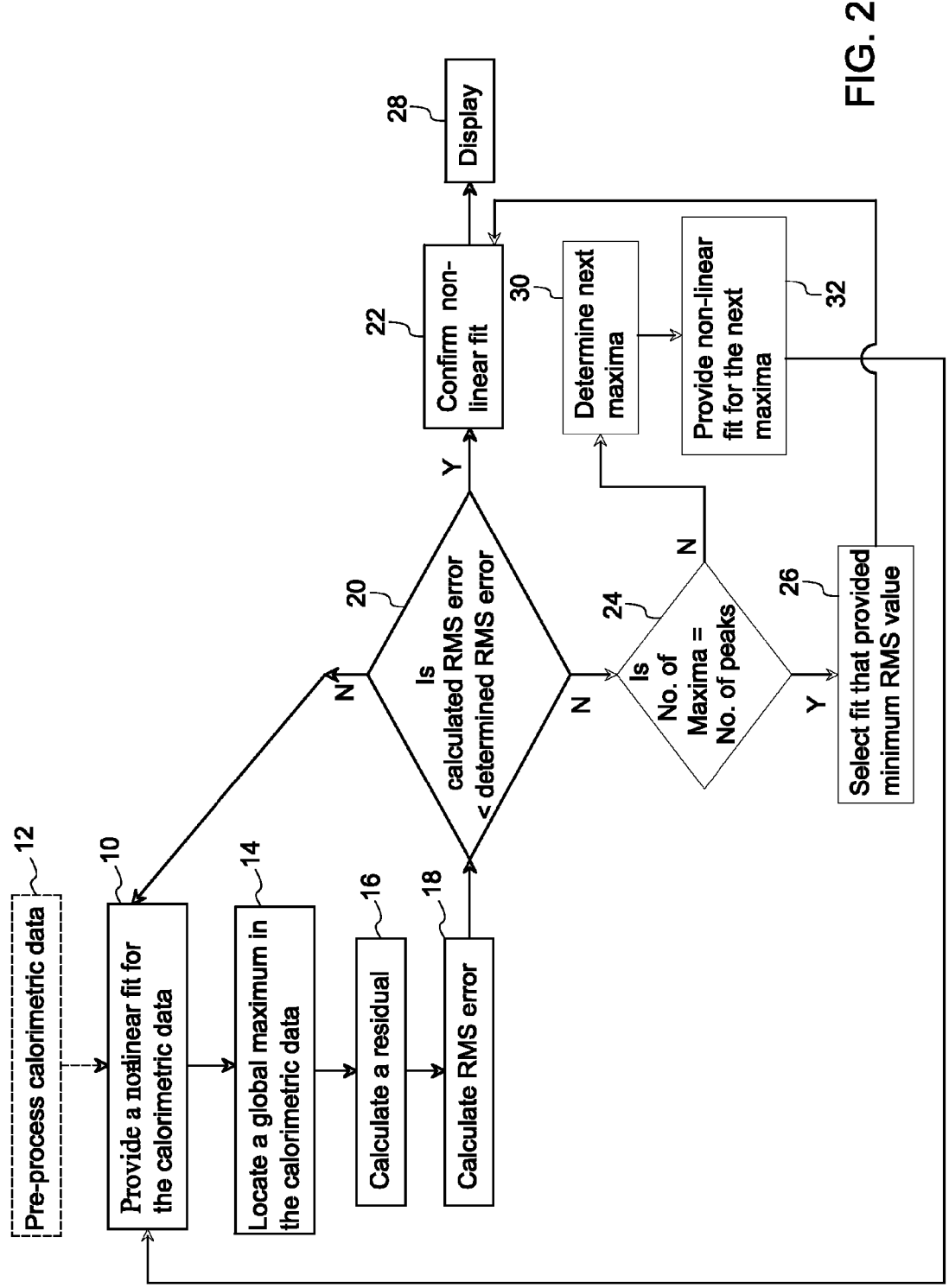
FIG. 2 is a flow chart for another example method for automatic peak fittings for calorimetric data.

In some embodiments, the algorithm may compare RMS values for different non-linear fits and decide the total number of peaks in the calorimetric data. In other embodiments, the user may input the number of maxima for the calorimetric data. As illustrated in FIG. 2, if the calculated RMS error is greater than the determined RMS, a second check may be performed for the non-linear fit at step 24, whereby the total number of peaks in the non-linear fit may be compared with the number of maxima inputted by the user. If the number of peaks in the non-linear fit is equal to the number of maxima, the non-linear fit may be selected. In embodiments where more than one non-linear fit have been attempted to be fitted in the calorimetric data, the non-linear fit having the minimum RMS error may be selected (step 26). The non-linear fit with the minimum RMS value may be then confirmed (step 22), and subsequently displayed (step 28). However, if the number of peaks in the non-linear fit is not equal to the number of maxima, e.g., if the number of peaks is less than the number of maxima, next peak may be determined in the calorimetric data (step 30). At step 32, a non-linear fit may be provided for the next maxima. The non-linear fit is provided for the next maxima while retaining the non-linear fit for the previous peak, i.e., the global maxima. Next, steps 10, 14, 16, 18 and 20 may be repeated whereby RMS error is calculated and compared to the determined RMS value until the RMS error is equal to or less than a determined RMS value. Optionally, the number of peaks may be updated in the system after every non-linear fit is confirmed. The non-linear fit is modified to fit a peak for the position corresponding to the next maximum residual while retaining the earlier identified peak location and shape.

The method may also comprise registering the peak locations for the determined peaks. The method may further comprise identifying peaks introduced due to impurities in the DSC sample. In one embodiment, the fitted peaks may be compared with an existing library of calorimetric events. The comparison may be used to identify events that may have been introduced due to impurities in the sample. In one example, the system may have built-in intelligence to identify and discard abnormally sharp peaks that usually occur due to presence of impurities in the sample. In another example, such ambiguities (sharp peaks) may be pre-fed in the system. The pre-fed information on ambiguities may be used to provide corrected information to the user regarding the calorimetric events.

Optionally, the information related to the calorimetric data is provided to the user. The data may be provided at different steps in the process. Alternatively or additionally, the final outcome may comprise textual as well as graphical representations of the number and locations of calorimetric peaks. The reporting may be performed in numerous ways, e.g., via a visual display terminal, a paper printout, or, indirectly for example, by outputting the parameter information to a database on a storage medium for later retrieval by a user. The reporting step may comprise reporting either textual or graphical information, or both. The parameters may be provided to the user by displaying the same on a display, or generating a printout of the parameters. Some methods of the invention may further comprise the action of extracting, from the model spectral parameters, information related to or inferred to be related to the physical functioning or operational state or an operational parameter of the sample and reporting such information to a user. Additional steps of comparing peak parameters (for instance, peak position) to a database and reporting, to a user, the calorimetric events and their corresponding temperature and time for one or more peaks may also be performed.

Figure 3:
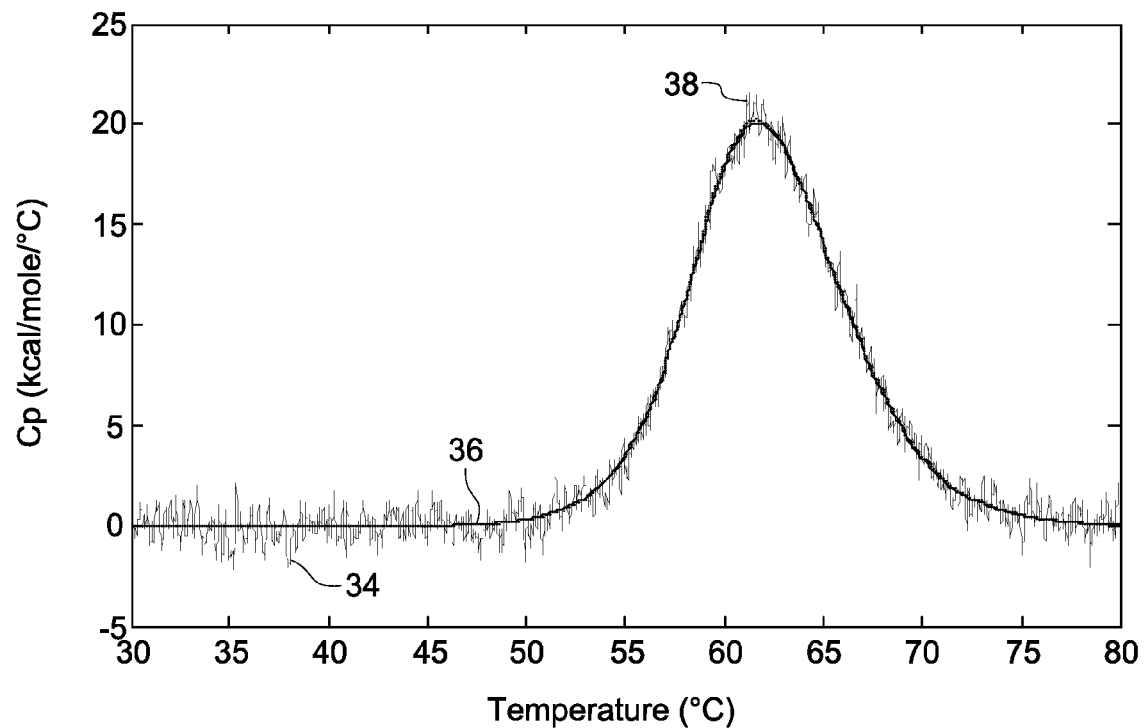
FIG. 3 is a graph of an example of calorimetric data for automatic peak fitting.
Figure 4:
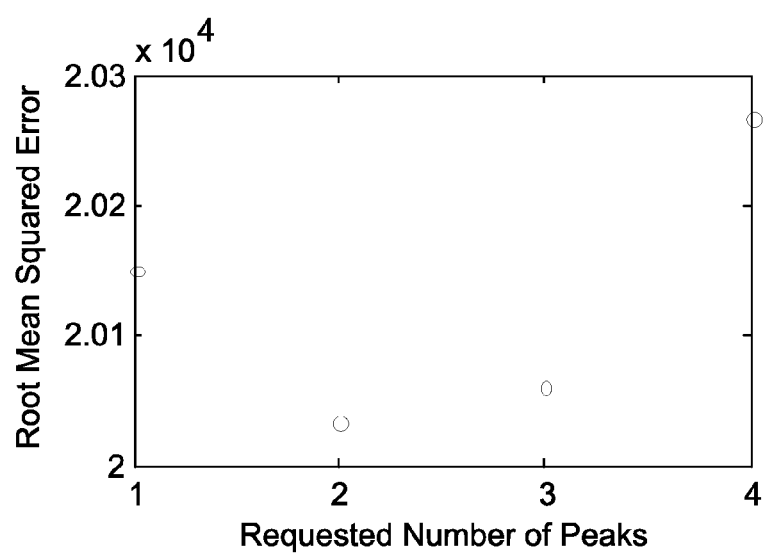
FIG. 4 is a graph for determining the RMS with regard to the number of peaks fitted in the calorimetric data of FIG. 3.

FIG. 3 illustrates an example of method of the invention. Calorimetric data represented by curve 34 is provided. A non-linear fit 36 is provided for the global maximum. A global maximum 38 is identified. RMS error is calculated and based on the RMS error a suitable non-linear fit is provided for the global maximum. Subsequently, if more than one peak exists, the subsequent peaks are non-linearly fitted using the iterations. As illustrated in FIG. 4, the least RMS error occurs for two peaks. The RMS value is higher for fitting one and three peaks, and the value of the RMS error increases as the number of peaks increases beyond two. Referring back to FIG. 3, the second peak is not easily visible to the human eye, however, using the method of the invention, the number of peaks is correctly identified as two.

FIG. 5 is an example of a

The methods of the invention may be applied in various applications where DSC is used. For example, the method may be used to study liquid crystals, or stability and/or optimum storage conditions for a material or compound for oxidation. In one example, the presence of an exothermic event may be used to assess the stability of a substance to heat. The method may be used for drug analysis in pharmaceutical and polymer industries, or for studying curing processes, which allows the fine tuning of polymer properties. The cross-linking of polymer molecules that occurs in the curing process is exothermic, resulting in a positive peak in the DSC curve that usually appears soon after the glass transition. In the pharmaceutical industry it is desirable to have well-characterized drug compounds in order to define processing parameters. For instance, if it is required to deliver a drug in the amorphous form, it is desirable to process the drug at temperatures below those at which crystallization can occur. The temperature range over which a mixture of compounds melts is dependent on their relative amounts. Consequently, less pure compounds will exhibit a broadened melting peak that begins at lower temperature than a pure compound. In a chemical analysis, the method may be used as an analysis tool to evaluate the purity levels of the samples.

The methods may be implemented in the existing software architecture with no modifications to hardware. Therefore, a more reliable, higher productivity calorimeter may be produced with no additional cost of goods.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method for automatically determining a position of one or more calorimetric peaks in a set of calorimetric data, comprising:
   a) providing a non-linear fit for the calorimetric data received from a calorimetric device;
   b) calculating a residual by subtracting the non-linear fit from the calorimetric data;
   c) calculating an error based on the residual;
   d) comparing the error with a predetermined error;
   e) providing another non-linear fit if the calculated error is greater than the predetermined error;
   f) determining whether another peak exists in the calorimetric data based on the calculated error; and
   g) displaying the non-linear fit for the calorimetric data on a visual display terminal.

2. The method of claim 1, further comprising, calculating a molar entropy change or an area occupied by the calorimetric data.

3. The method of claim 1, wherein calculating the error comprises calculating a root mean square error.

4. The method of claim 1, further comprising, determining a position of a maximum residual of the calorimetric data.

5. The method of claim 1, comprising inputting a determined number of peaks.

6. The method of claim 1, wherein the non-linear fit comprises a polynomial fit, or a Levenberg-Marquardt algorithm.

7. The method of claim 1, further comprising displaying the non-linear fit at various stages.

8. The method of claim 1, further comprising repeating steps b) through f).

9. The method of claim 1, further comprising determining a number of peaks in the calorimetric data.

10. The method of claim 4, further comprising automatically comparing the maximum residual position with a library of calorimetric data.

11. The method of claim 4, further comprising registering a position of the maximum residual.

12. The method of claim 10, comprising accepting or rejecting the calculated data based on the comparison with the library of calorimetric data.

13. The method of claim 11, comprising displaying associated physical phenomenon.

* * * * *